US 8,444,549 B2

(12) United States Patent
Viola et al.

(10) Patent No.: US 8,444,549 B2
(45) Date of Patent: May 21, 2013

(54) SELF-STEERING ENDOSCOPIC DEVICE

(75) Inventors: Frank Viola, Sandy Hook, CT (US); Eric Taylor, East Hampton, CT (US)

(73) Assignee: Covidien LP, Mansfield, MA (US)

( * ) Notice: Subject to any disclaimer, the term of this patent is extended or adjusted under 35 U.S.C. 154(b) by 485 days.

(21) Appl. No.: 12/756,724

(22) Filed: Apr. 8, 2010

(65) Prior Publication Data
US 2010/0268030 A1 Oct. 21, 2010

Related U.S. Application Data

(60) Provisional application No. 61/169,918, filed on Apr. 16, 2009.

(51) Int. Cl.
*A61B 1/01* (2006.01)

(52) U.S. Cl.
USPC .................. 600/117; 600/145; 600/146

(58) Field of Classification Search
USPC .................. 600/114, 117, 145, 156
See application file for complete search history.

(56) References Cited

U.S. PATENT DOCUMENTS

| | | | |
|---|---|---|---|
| 3,674,014 A | 7/1972 | Tillander | |
| 4,292,691 A * | 10/1981 | Forrest et al. | 2/65 |
| 4,366,810 A * | 1/1983 | Slanetz, Jr. | 600/117 |
| 4,469,091 A * | 9/1984 | Slanetz, Jr. | 600/117 |
| 4,753,223 A | 6/1988 | Bremer | |
| 4,832,473 A | 5/1989 | Ueda | |
| 5,334,207 A | 8/1994 | Gay, Jr. | |
| 5,643,175 A | 7/1997 | Adair | |
| 6,015,414 A | 1/2000 | Werp et al. | |
| 6,485,409 B1 | 11/2002 | Voloshin et al. | |
| 6,527,782 B2 | 3/2003 | Hogg et al. | |
| 6,772,001 B2 | 8/2004 | Maschke | |
| 6,984,203 B2 | 1/2006 | Tartaglia et al. | |
| 6,988,988 B2 | 1/2006 | Voloshin et al. | |
| 2002/0111535 A1 | 8/2002 | Kim et al. | |
| 2003/0055411 A1 | 3/2003 | Whitman et al. | |
| 2003/0105386 A1 | 6/2003 | Voloshin et al. | |
| 2004/0092962 A1 | 5/2004 | Thornton et al. | |
| 2004/0215057 A1 | 10/2004 | Wellman et al. | |
| 2005/0004644 A1 | 1/2005 | Kelsch et al. | |
| 2005/0187576 A1 | 8/2005 | Whitman et al. | |
| 2005/0203382 A1 | 9/2005 | Govari et al. | |
| 2006/0004254 A1 | 1/2006 | Voloshin et al. | |
| 2006/0063973 A1 | 3/2006 | Makower et al. | |
| 2007/0038293 A1 | 2/2007 | St. Goar et al. | |
| 2011/0268030 A1* | 11/2011 | Fujita | 370/328 |

* cited by examiner

*Primary Examiner* — W B Perkey

(57) ABSTRACT

An endoscopic device including mechanisms to facilitate insertion of the device is disclosed. The device includes a sensing assembly configured for determining the position of the distal end of the device relative to a lumen. The device may further including a steering mechanism configured to direct the distal end of the device. A controller may be operably connected to the sensing assembly and the steering mechanism. The controller may be incorporated into the endoscopic device. Alternately, the controller may be positioned remote of the endoscopic device.

22 Claims, 7 Drawing Sheets

SELF-STEERING ENDOSCOPIC DEVICE

CROSS-REFERENCE TO RELATED APPLICATIONS

This application claims the benefit of and priority to U.S. Provisional Patent Application No. 61/169,918, filed Apr. 16, 2009, the entire disclosure of which is incorporated by reference herein.

BACKGROUND

1. Technical Field

The present disclosure relates to generally to endoscopes and endoscopic procedures. More particularly, the present disclosure relates to an apparatus and method for facilitating insertion of a flexible endoscope along a tortuous path, such as for colonoscopic examinations and treatment.

2. Background of Related Art

Endoscopic devices are used in a variety of different diagnostic and interventional procedures, including colonoscopy, bronchoscopy, thoracoscopy, laparoscopy and video endoscopy.

For example, in a colonoscopy a flexible endoscopic device is inserted into a patient's colon for diagnostic examination and/or surgical treatment of the colon. The endoscopic device may include a fiberoptic imagining bundle or a miniature camera located at the distal tip. The device may further include one or more instrument channels that may be used for insufflation or irrigation, air and water channels, and vacuum channels. The endoscopic device is inserted via the patient's anus and is advanced through the colon, allowing direct visual examination of the colon, the ileocecal valve and portions of terminal ileum.

Insertion of the endoscopic device is complicated by the fact that the gastrointestinal tract represents a tortuous and convoluted path. Considerable manipulation of the endoscopic device is often necessary to advance the endoscopic device through the tract, making the procedure more difficult and time consuming and adding to the potential for complications, such as intestinal perforation. Steerable colonscopes and other endoscopic devices have been devised to facilitate selection of the correct path through the curves of the gastrointestinal tract. Various steerable endoscopes, catheters and insertion devices for medical examination or treatment are described in U.S. Pat. Nos. 4,543,090; 5,337,732; 5,383,852; 5,487,757; 5,624,381; 5,662,587; and 5,759,151 and in U.S. Patent Application Publication No. 2006/0089531. However, in each of these devices a user is required to visualize the position of the operative end of the device relative to the lumen wall and manually guide the device to the desired location within the gastrointestinal tract.

It would therefore be beneficial to have an endoscopic device capable of sensing its position within a lumen and steering itself to a desired location.

SUMMARY

Provided is an endoscopic device configured for insertion into a lumen. The device includes an elongated tubular body, a guide member extending distally from said elongated tubular body, and a sensing assembly operably affixed to the guide member and configured for sensing the location of the guide member relative to a lumen. The sensing member includes a plurality of sensors. The sensors may be radially spaced about the guide member. The sensors may also be radially spaced about the guide member.

The sensing assembly is configured to measure an electrical property between any two sensors in the plurality of sensors. The sensors may be configured to measure the conductance, capacitance or resistance between at least two of the sensors and or one sensor and a patient ground. The sensing assembly may be operably connected to a controller. Alternatively, the sensing assembly may include a plurality of mechanically activated sensors. The mechanically activated sensors may include bubble buttons, microswitches and the like.

The endoscopic device may further including a steering mechanism operably situated between the elongated tubular body and the guide member. The steering mechanism may be operably connected to the sensing assembly. The steering mechanism is configured to position the guide member relative to the elongated tubular body. The steering mechanism may include a plurality of magnetic members and a plurality of corresponding magnets. The magnets are configured to be selectively activated. Activation of one of the magnets causes the guide member to flex in a first direction relative to the tubular body. Activation of a second of the magnets causes the guide member to flex in a second direction relative to the tubular body. The steering mechanism may instead include alternate mechanical means, such as, push-pull cables, FLEXINOL manufactured by Dynalloy, Inc. (Costa Mesa, Calif.), lead screw, or other suitable device.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
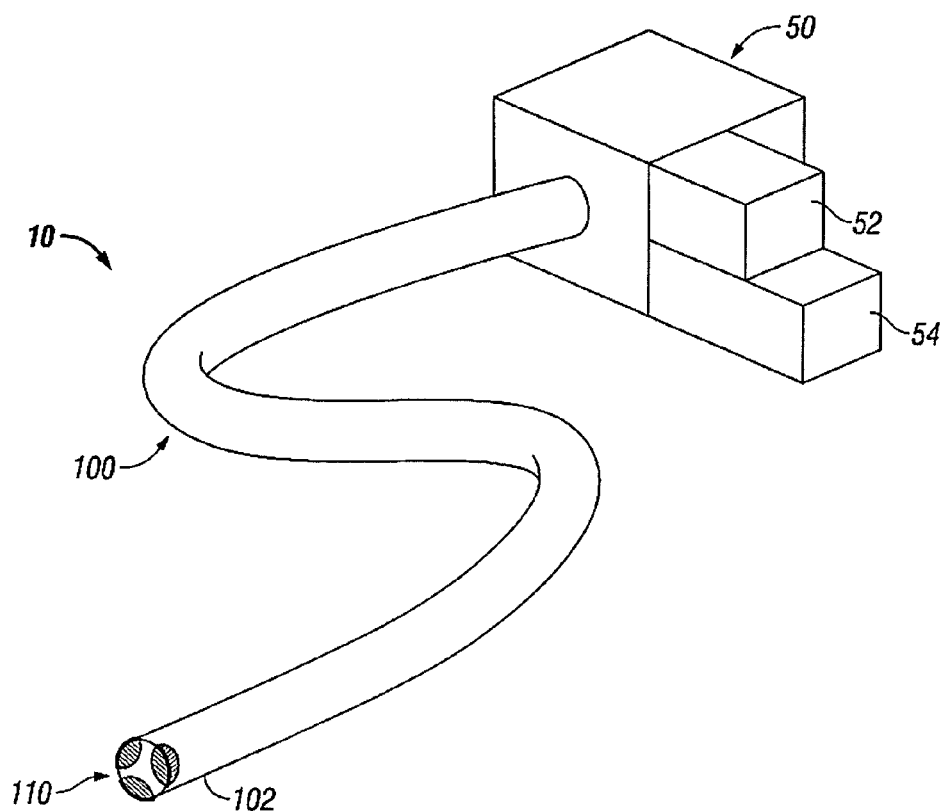
FIG. 1 is a perspective view of an endoscopic system according to an embodiment of the present disclosure.

Embodiments of the presently disclosed endoscopic device will now be described in detail with reference to the drawings, in which like reference numerals designate identical or corresponding elements in each of the several views. Although the embodiments of the present disclosure will be described as relates to colonoscopies, it is envisioned that the aspects of the present disclosure may be applied to devices for any endoscopic procedure.

Figure 2:
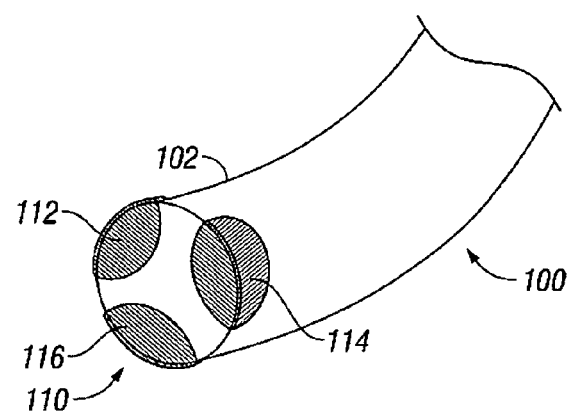
FIG. 2 is an enlarged prospective view of the distal end of the endoscopic device of the endoscopic system of FIG. 1.

Referring initially to FIGS. 1 and 2, an endoscopic system according to an embodiment of the present disclosure is shown generally as endoscopic system 10. Endoscopic system 10 includes an endoscopic device 100 operably connected to a control unit 50. As will be discussed in further detail below, endoscopic device 100 includes a sensing assembly 110 for determining the orientation and position of endoscopic device 100 within a lumen, i.e. colon. Endoscopic device 100 further includes a steering mechanism (not shown) for guiding endoscopic device 100 through the lumen. The steering mechanism may include any suitable means for selectively controlling the movement of distal end 102 of endoscopic device 100, and is not limited to the embodiments disclosed herein.

Control unit 50 is operably connected to endoscopic device 100. Control units for operating endoscopic devices are known. Control unit 50 includes a controller 52 operably connected to sensing assembly 110 and the steering mechanism (not shown) for guiding endoscopic device 100 through a lumen. Control unit 50 may include connections (not shown) for connecting endoscopic device 100 with fluid and/or gas sources (not shown), optical devices (not shown), and/or other apparatus (not shown) useful in endoscopic procedures. Control box 50 may further include a drive mechanism 54 for axially advancing and/or retracting endoscopic device 100 during an endoscopic procedure. Alternatively, endoscopic device 100 may be axially advanced and/or retracted manually by a user or users.

Figure 3:
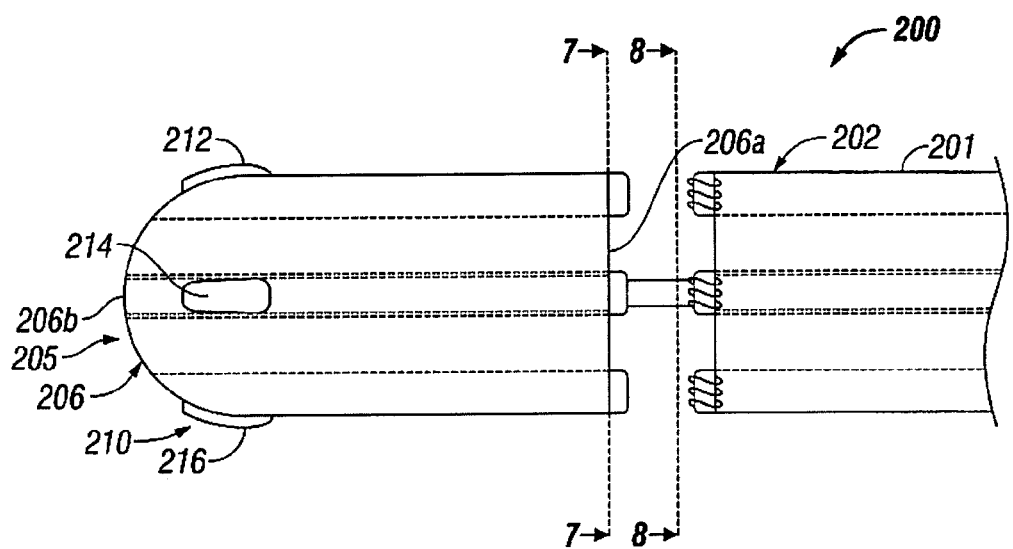
FIGS. 3-5 are enlarged side views of the distal end of an endoscopic device according to another embodiment of the present disclosure, in an initial position (FIG. 3), in a first flexed position (FIG. 4) and in a second flexed position (FIG. 5)
Figure 4:
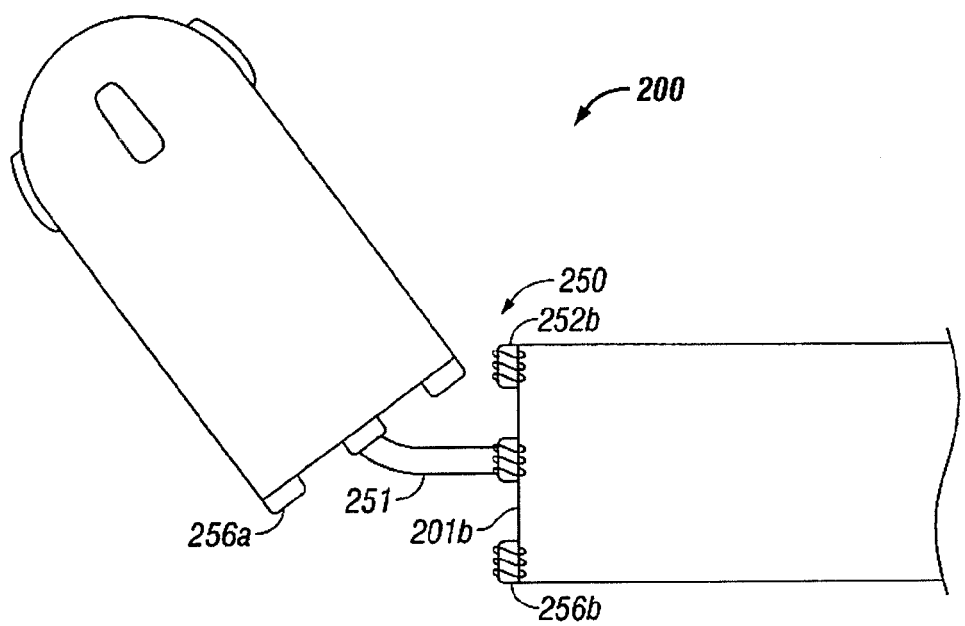
Figure 5:
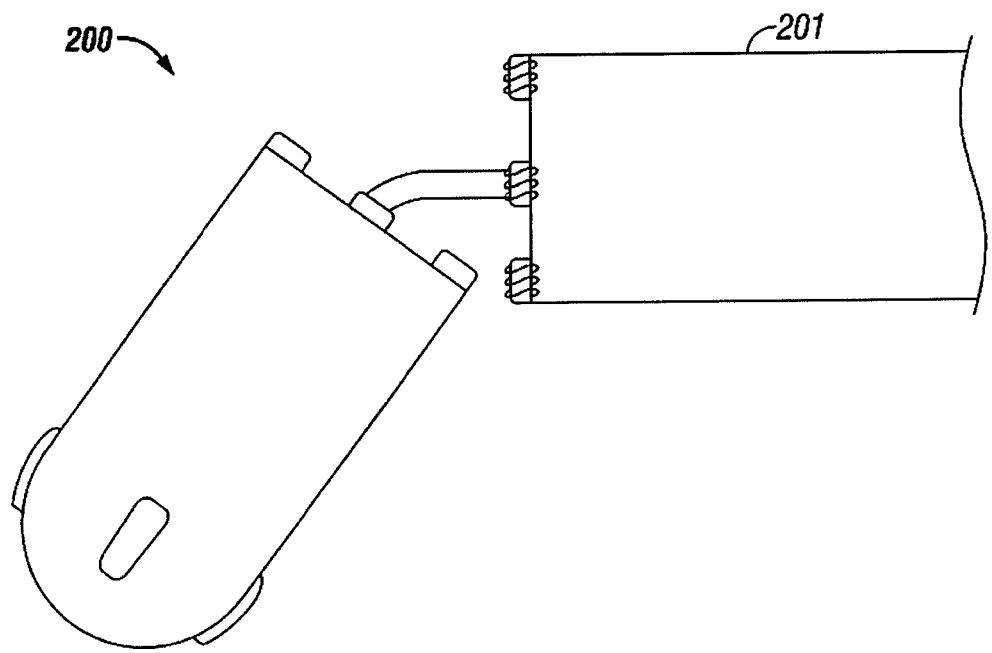
Figure 6:
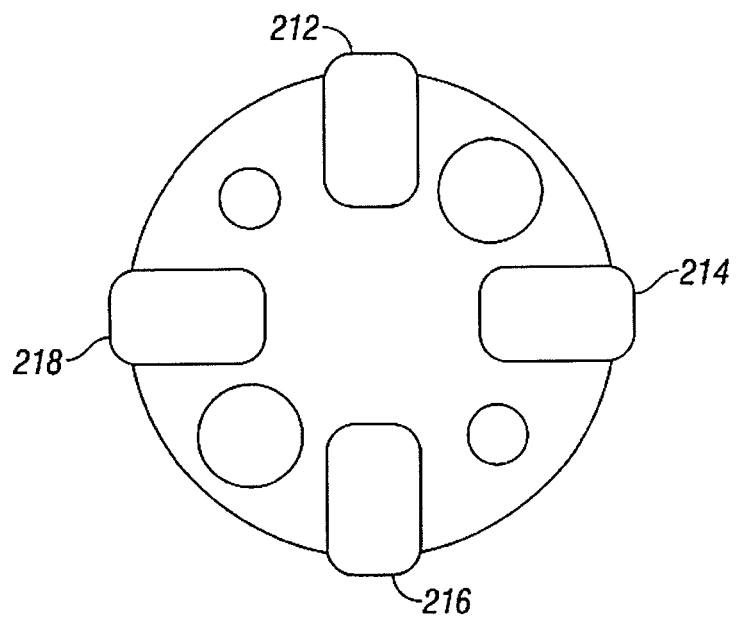
FIG. 6 is an enlarged end view of the distal end of the endoscopic device of FIGS. 3-5.
Figure 7:
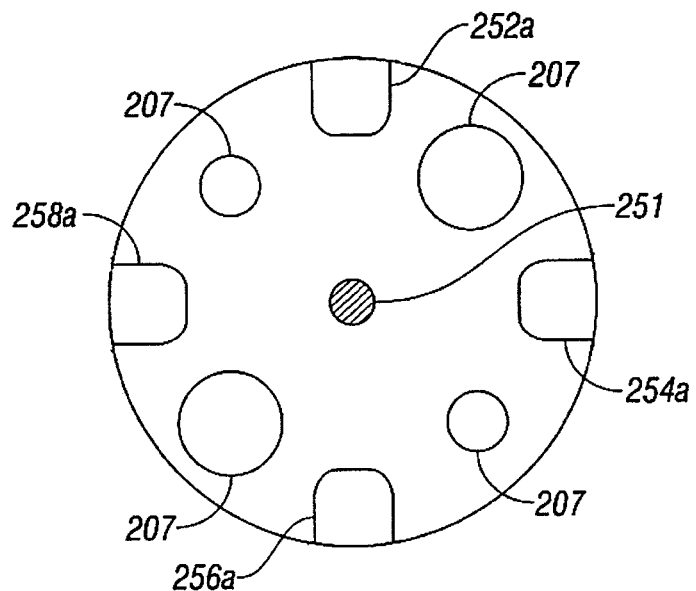
FIG. 7 is an enlarged end view of the endoscopic device of FIG. 3 taken along line 7-7.
Figure 8:
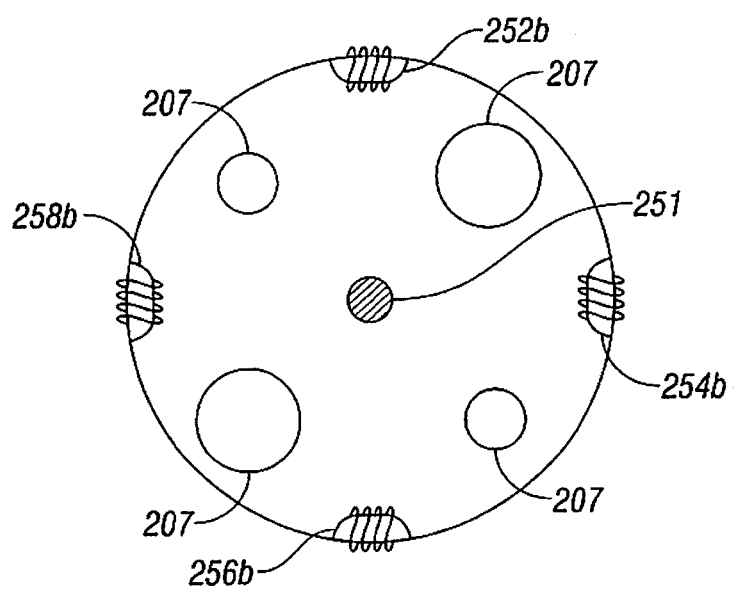
FIG. 8 is an enlarged end view of the endoscopic device of FIGS. 3-7 taken along line 8-8 of FIG. 3.
Figure 9:
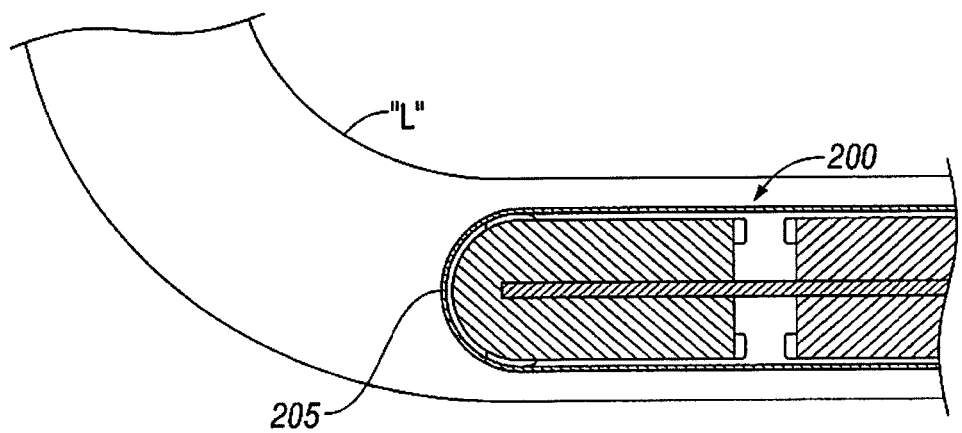
FIGS. 9-12 are cross-sectional side views of the endoscopic device of FIGS. 3-8 in various positions along a lumen "L"

Sensing assembly 110 is operably mounted to a distal end 102 of endoscopic device 100. Sensing assembly 110 includes a plurality of sensors 112, 114, 116. Although as shown, endoscopic device 100 includes three sensors, the number and placement of the sensors may vary. Sensors 112, 114, 116 are radially spaced about and extend proximally over distal end 102 of endoscopic device 100. Sensors 112, 114, 116 are sized and positioned such that fewer than all of sensors 112, 114, 116 contact a portion of a lumen as endoscopic device 100 is inserted therethrough. Sensors 112, 114, 116 are operably connected to controller 52 of control unit 50. Alternatively, controller 52 may be located within guide member 205 (FIG. 3) and/or tubular body 201. Sensors 112, 114, 116 and controller 52 may be configured to measure conductance, resistance, capacitance or another suitable electrical property between sensors 112, 114, 116 and/or between sensors 112, 114, 116 and a lumen "L" (FIG. 9). As will be discussed in further detail below, the position of distal end 102 of endoscopic device 100 relative to the lumen may be determined using the electrical values measured between sensors 112, 114, 116 and the lumen. Alternatively, sensors 112, 114, 116 may be configured with a mechanical interface, e.g. bubble button (not shown). In this manner, the position of distal end 102 of endoscopic device 100 within a lumen may be determined when only a single sensor 112, 114, 116 contacts the lumen.

Referring now to FIGS. 3-8, an alternate embodiment of an endoscopic device according to the present is shown generally as endoscopic device 200. Endoscopic device 200 is substantially similar to endoscopic device 100 and will only be described as it relates to the differences therebetween. Endoscopic device 200 includes a substantially elongated tubular body 201 configured to be inserted into a lumen through the mouth or anus. Endoscopic device 200 includes a guide member 205 extending from a distal end 202 thereof. As will also be discussed in further detail below, endoscopic device 200 also includes a steering mechanism 250 operably connected to guide member 205 for controlling the position of guide member 205 relative to tubular body 201.

As shown, guide member 205 includes a substantially cylindrical body 206 having a substantially rounded distal end 206b and a flat proximal end 206a. The length of body 206 may vary depending on the configuration of the lumen being inspected. Distal end 206b of guide member 205 is configured to be inserted through a lumen in a non-traumatic manner. As will be discussed in further detail below, a sensing assembly 210 is mounted on a body 206 of guide member 205. Guide member 205 may include any number of openings or channels 207. Openings 207 extend into and through tubular body 201 and may be configured to receive a scope or other endoscopic devices and/or to provide irrigation fluid and/or suction to distal end 202 of endoscopic device 200.

Still referring to FIGS. 3-8, sensing assembly 210 includes sensors 212, 214, 216, 218 extending about rounded distal end 206b of extension 205. Although four sensors are shown, it is envisioned that the aspects of the present disclosure may be adapted for use with more or less than four sensors. It is further envisioned that the plurality of sensors may be mounted to distal end 206b of guide member 205 in unlimited number of configurations. Sensors 212, 214, 216, 218 are operably connected to controller 52 (FIG. 1) and are configured to measure one or more electrical properties, i.e. conductance, capacitance or resistance, between sensors 212, 214, 216, 218, and/or between sensors 212, 214, 216, 218 and a lumen. As discussed above, the electrical properties measured between sensors 212, 214, 216, 218 will vary depending on the position of guide member 205 in relation to lumen. The greater the contact or proximity between sensors 212, 214, 216, 218 and the lumen the greater the effect on the measured electrical properties between respective sensors 212, 214, 216, 218. These differences in the measured electrical properties may be used to determine the relative position of guide member 205 within the lumen. As will be discussed in further detail below, once the position of guide member 205 relative to the lumen is known, steering mechanism 250 may adjust guide member 205 accordingly to guide distal end 202 of endoscopic device 200 away from contact with the lumen wall and towards the center of the lumen.

Steering mechanism 250 is included in distal end 202 of endoscopic device 200 and is configured to move guide member 205 relative to tubular body 201. Steering mechanism 250 includes a flexible shaft 251, magnetic members 252a, 254a, 256a, 258a mounted to proximal end 205a of guide member 205, and electro-magnets 252b, 254b, 256b, 258b mounted to a distal end 201b of tubular body 201. Magnetic members 252a, 254a, 256a, 258a may include fixed magnets, electro-magnets, iron or other suitable magnetic material, and any combination thereof. In an alternative embodiment, magnetic members 252a, 254a, 256a, 258a are mounted to distal end 201b of tubular body 201 and electro-magnets 252b, 254b, 256b, 258b are mounted to proximal end 205a of guide member 205. Although steering mechanism 250 is described has having four electro-magnets and corresponding magnetic members; it is envisioned that steering mechanism 250 may include any number of magnets and any number of magnetic members. Steering mechanism 250 is configured to be operably connected to controller 52. Although steering mechanism 250 is shown and described herein in combination with sensing assembly 210, it is envisioned that steering mechanism 250 may be operated without sensing assembly 210. It is further envisioned that steering mechanism 250 may be controlled manually by an operator.

With reference still to FIGS. 3-8, flexible shaft 251 of steering mechanism 250 extends between tubular body 201 and guide member 205 and is configured to permit guide member 205 to move relative to tubular body 201. Flexible shaft 251 is operably connected to control unit 50. Control unit 50 is configured to extend or retract guide member 205 relative to tubular body 201 as distal end 202 of endoscopic device 200 is guided through lumen "L". Alternatively, shaft 251 may extend a fixed length from tubular body 201, thereby maintaining guide member 205 a fixed distance relative to tubular body 201.

Magnetic members 252a, 254a, 256a, 258a are substantially rectangular bodies composed of magnetically sensitive material. Magnetic members 252a, 254a, 256a, 258a are radial positioned about proximal end 205a of guide member 205. Magnetic members 252a, 254a, 256a, 258a, may, as shown, extend distally from guide member 205, or instead, may be recessed within guide member 205. Magnetic members 252a, 254a, 256a, 258a may instead be mounted on distal end 201b of tubular body 201. In an alternate steering mechanism 250 may include two sets of magnets instead of magnetic members.

Magnets 252b, 254b, 256b, 258b are substantially rectangular bodies radial positioned about distal end 201b of tubular body 201 in alignment with magnetic members 252a, 254a, 256a, 258a. Magnets 252b, 254b, 256b, 258b may extend distally from tubular body 201 or, instead, may be recessed therein. Magnets 252b, 254b, 256b, 258b are operably connected to controller 52 (FIG. 1) and are configured to be selectively activated as endoscopic device 200 is longitudinally advanced through lumen "L". In one embodiment, magnets 252b, 254b, 256b, 258b are electromagnetic, and as such are capable of selectively attracting or repelling respective magnetic members 252a, 254a, 256a, 258a.

The operation of endoscopic device 200 will now be described with reference to FIGS. 9-12. Although the operation of endoscopic device 200 will be described with reference to a two dimensional field, it is appreciated that endoscopic device, and more particularly sensing assembly 210 and steering mechanism 250 operate in three dimensional space.

Prior to or upon insertion of distal end 202 of endoscopic device 200 into a lumen "L", the lumen is insufflated with insufflation gas. In this manner, distal end 202 of endoscopic device 200 may be axially advanced through lumen "L" with reduced contact with the lumen wall. Prior to use, endoscopic device 200 may be covered in a protective sheath 200a. Sheath 200a may be disposable and may be composed of a transparent material.

Referring initially to FIG. 9, as distal end 202 of endoscopic device 200 advances through lumen "L" guide member 205 is preferably maintained in the center of lumen "L". As long as guide member 205 remains centered within lumen "L", none of sensors 212, 214, 216, 218 contact lumen "L" and guide member 205 is maintained in longitudinal alignment with tubular body 201. Equal repulsion between magnetic members 252a, 254a, 256a, 258a and respective magnets 252b, 254b, 256b, 258b maintains guide member 205 in longitudinal alignment with tubular member 201.

Figure 10:
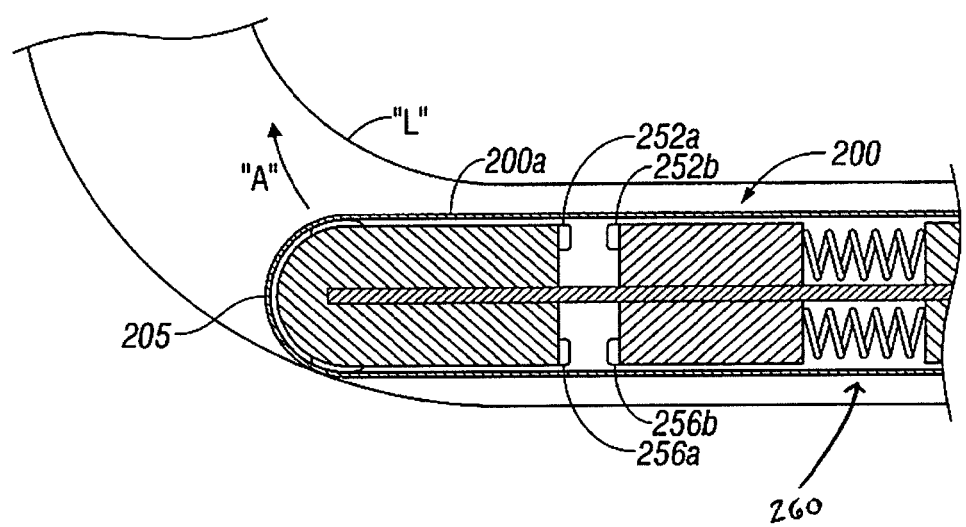

Turning now to FIG. 10, as a portion of guide member 205 approaches or comes into contact with lumen "L", one or more of sensors 212, 214, 216, 218 mounted on guide member 205 also contact lumen "L". The position of guide member 205 relative to lumen "L" may be determined using the electrical properties measured between respective sensors 212, 214, 216, 218. Controller 52 analyzes the one or more of the electrical properties between sensors 212, 214, 216, 218, and from this information is able to determine the position of guide member 205 relative to lumen "L".

For example, if the resistance measured between sensor 212 and sensor 214 less than the resistance measured between sensor 212 and sensors 216, 218, controller 52 will determine that the center of lumen "L" is in the direction of sensors 212, 214. Conversely, if the resistance measure between sensor 212 and sensor 214 is greater than the resistance measured between sensors 212 and sensors 216, 218, controller 52 will determine that the portion of guide member 205 including sensors 212, 214 is close to and/or in contact with lumen "L". An equal measurement between each of sensors 212, 214, 216, 218 indicates that guide member 205 is not in contact with lumen "L" and may be safely advanced therethrough. Alternatively, when sensors 212, 214, 216, 218 are mechanically activated, contact of a single sensor 212, 214, 216, 218 with lumen "L" indicates to controller 52 the relative position of guide member 205.

Figure 11:
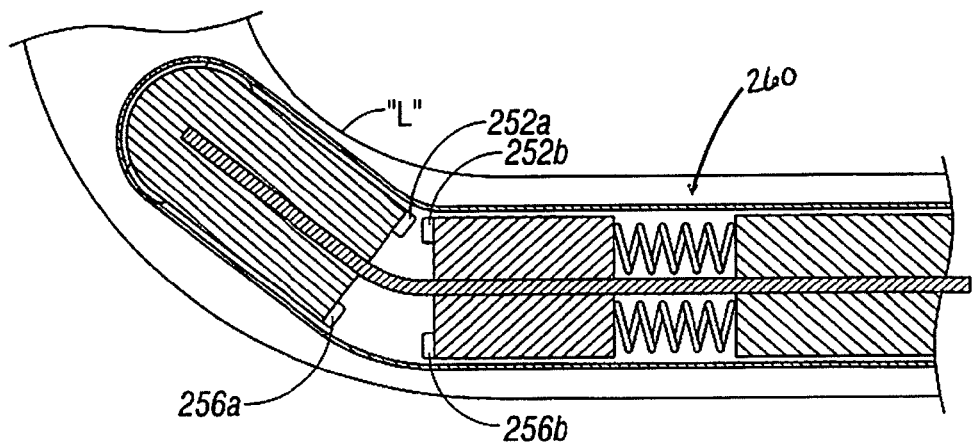
Figure 12:
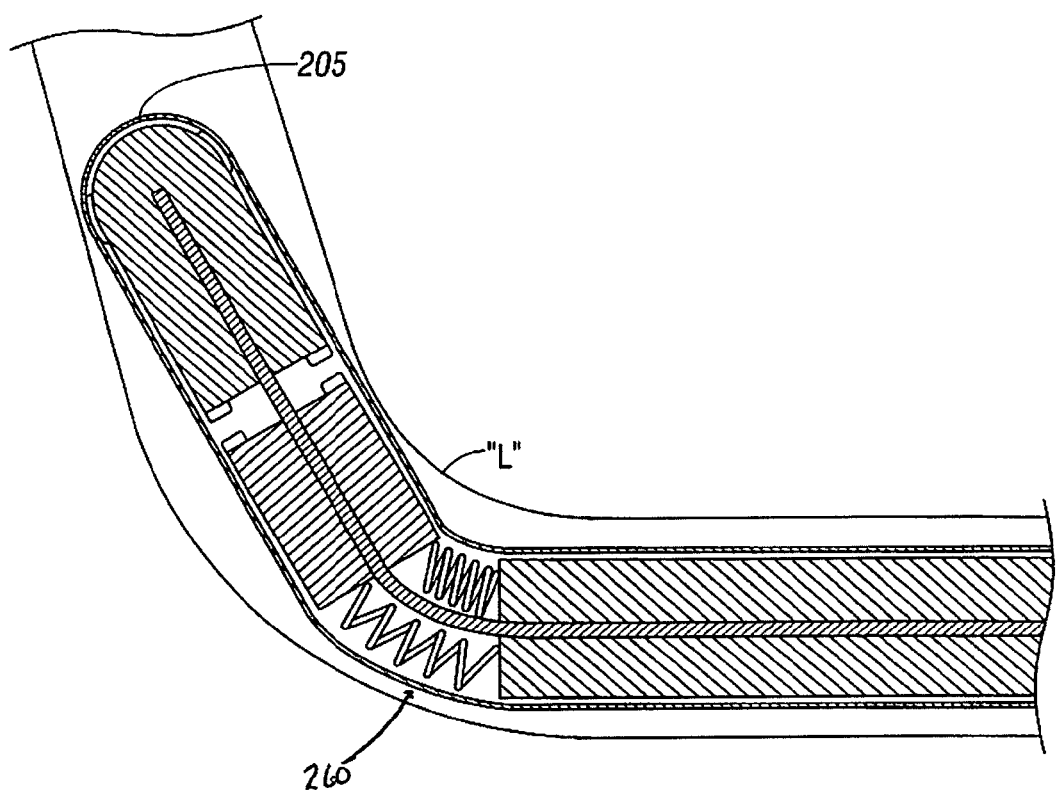

Once the position of guide member 205 relative to lumen "L" is determined, steering mechanism 250 may be activated to steer guide member 205 towards the center of lumen "L". As shown in FIGS. 10 and 11, contact of guide member 205 with lumen "L" is registered by controller 52 (FIG. 1), thereby activating steering mechanism 250 to flex guide member 205 in the direction of arrow A and away from the lumen "L". This may be accomplished in a number of ways. With reference still to FIG. 11, magnet 252b may be activated to attract magnetic member 252a, magnet 256b may be activated to repel magnetic member 256a, or a combination of attraction and repulsion. In any of these manners, shaft 251 flexes under the force of the magnets 252b, 256b, thereby repositioning guide member 205 relative to tubular body 201 and directing distal end 202 of endoscopic device 200 towards the center of lumen "L". As discussed above, endoscopic device 200 may include a variety of steering mechanisms capable of manipulating guide member 205 relative to tubular body 201, and should not be limited to steering mechanism 250. Endoscopic device 200 may further include one or more flex regions 260 along the length thereof. Flex regions 260 are configured to permit flexion of endoscopic device 200 proximal of guide member 205.

As discussed above, when the measured electrical properties between sensors 212, 214, 216, 218 are balanced, it indicates that guide member 205 is no longer in contact with lumen "L". To maintain this position, controller 52 activates steering mechanism 250 do realign guide member 205 and tubular body 201. As discussed above, shaft 251 may be configured such that once magnets 252b, 256b are deactivated guide member 205 will flex back to an aligned position. Alternatively, magnets 252b, 254b, 256b, 258b may be activated equally to maintain guide member 205 in the axially aligned position.

This process may be repeated as needed during an endoscopic procedure. Endoscopic device 200 may be configured for connection to an imaging device, i.e. ultrasound or optical, for monitoring the progress of endoscopic device 200 as it is inserted and removed from a patient. Endoscopic device 200 may include a tag or marker (not shown) for improving the visibility of distal end 202 of endoscopic device 200. Additionally, controller 52 include a mapping program configured to map the path taken by endoscopic device 200 as it is inserted into a lumen "L". Controller 52 may use the generated map to control the movement of guide member 205 as endoscopic device 200 is removed from lumen "L", thereby increasing the speed and efficiency in which the endoscopic procedure may be completed. By generating a map to control the movement of guide 205, reinsertion of endoscopic device 200 is also made easier.

Figure 13:
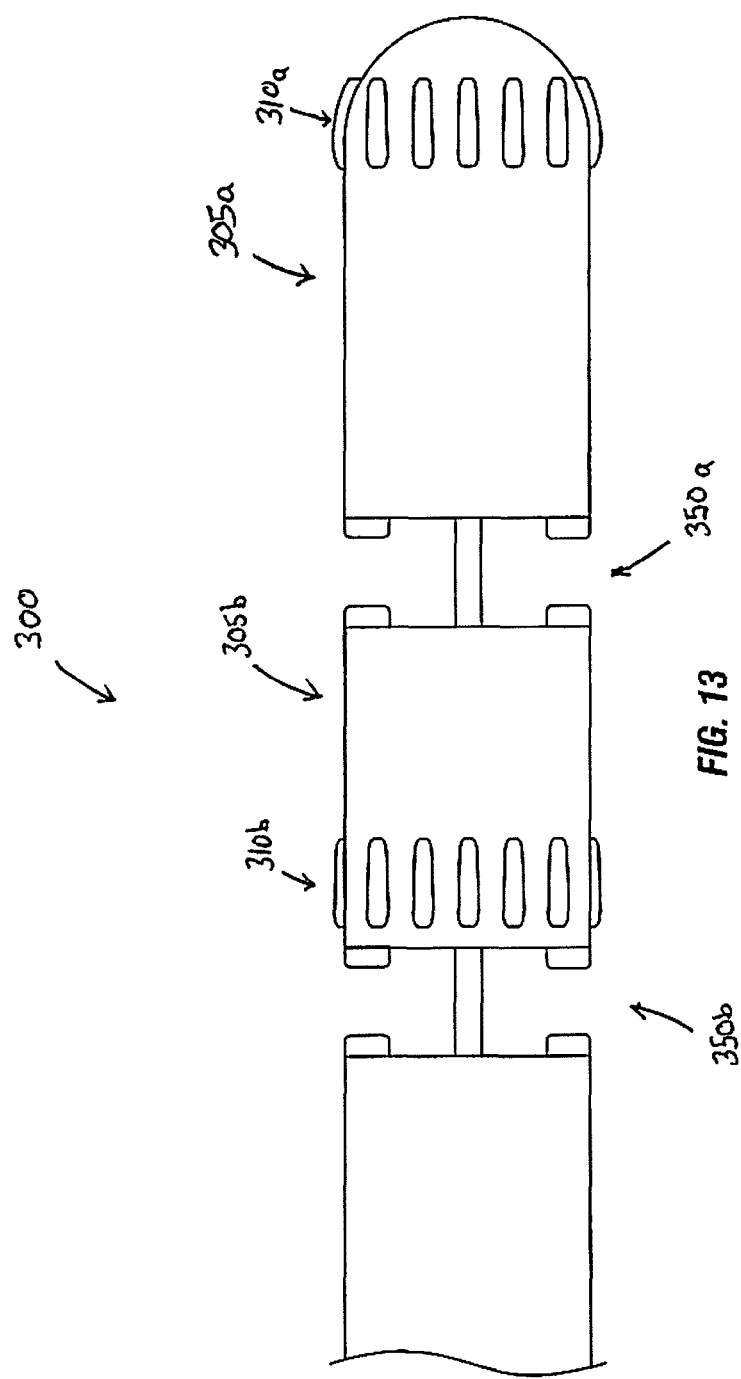
FIG. 13 is an enlarged view of the distal end of an alternate guide member according to an embodiment of the present disclosure.

With reference now to FIG. 13, an alternate embodiment of the distal end of an endoscopic device according to the present disclosure is shown generally as endoscopic device 300. Endoscopic device 300 includes a first guide member 305a and a second guide member 305b. Guide member 305a is substantially similar to guide member 205 discussed hereinabove, Guide member 305b positioned proximal of guide member 305b and is configured to move endoscopic device 300 in combination with guide member 305. Endoscopic device 300 further includes first and second steering mechanism 350a, 350b. As discussed above, steering mechanism 350a, 350b may include any suitable mechanism for moving first and second guide members 305a, 305b.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An endoscopic device comprising:
   an elongated tubular body;
   a guide member extending distally from said elongated tubular body; and
   a sensing assembly operably affixed to said guide member and configured for sensing the location of said guide member relative to a lumen, wherein said sensing assembly includes a plurality of sensors configured to measure at least one of conductance, capacitance, resistance and proximity between at least two of said plurality of sensors.

2. The endoscopic device of claim 1, wherein the sensors are spaced about said guide member.

3. The endoscopic device of claim 1, wherein the sensors are radially spaced about said guide member.

4. The endoscopic device of claim 1, wherein the sensing assembly is configured to measure an electrically property between any two of said plurality of sensors.

5. The endoscopic device of claim 1, wherein the sensing assembly is configured to measure an electrically property between any one of said plurality of sensors and the lumen.

6. The endoscopic device of claim 1, wherein said sensing assembly is operably connected to a controller.

7. The endoscopic device of claim 1, wherein said sensing assembly includes a plurality of mechanically activated sensors.

8. The endoscopic device of claim 1, further including a steering mechanism operably situated between said elongated tubular body and said guide member.

9. The endoscopic device of claim 8, wherein said steering mechanism is operably connected to said sensing assembly.

10. The endoscopic device of claim 9, wherein said steering mechanism is configured to position said guide member relative to said elongated tubular body.

11. The endoscopic device of claim 8, wherein said steering mechanism includes a plurality of magnetic members and a plurality of corresponding magnets.

12. The endoscopic device of claim 11, wherein said plurality of magnets are configured to be selectively activated.

13. The endoscopic device of claim 12, wherein activation of one of said plurality of electro-magnets causes said guide member to flex in a first direction relative to said tubular body.

14. The endoscopic device of claim 13, wherein activation of a second of said plurality of magnets causes said guide member to flex in as second direction relative to said tubular body.

15. The endoscopic device of claim 1, further including a second sensor mechanism.

16. An endoscopic device comprising:
   an elongated tubular body;
   a guide member extending distally from said tubular body; and
   a steering mechanism operably connected to said elongated tubular body and said guide member for moving said guide member relative to said elongated tubular body, wherein said steering mechanism includes a plurality of magnetic members and a plurality of corresponding magnets.

17. The endoscopic device of claim 16, wherein said steering mechanism is configured to position said guide member relative to said elongated tubular body.

18. The endoscopic device of claim 16, wherein said plurality of electro-magnets are configured to be selectively activated.

19. The endoscopic device of claim 16, wherein activation of one of said plurality of electro-magnets causes said guide member to flex in a first direction relative to said tubular body.

20. The endoscopic device of claim 19, wherein activation of a second of said plurality of magnets causes said guide member to flex in a second direction relative to said tubular body.

21. The endoscopic device of claim 16, further including a sensing member having a plurality of sensors.

22. The endoscopic device of claim 16, further including a sensing assembly mounted on said guide member.

* * * * *